(12) United States Patent
Gindele et al.

(10) Patent No.: US 11,933,485 B2
(45) Date of Patent: Mar. 19, 2024

(54) HERMETICALLY SEALED LED LIGHT AND METHOD FOR MANUFACTURING A HERMETICALLY SEALED LED LIGHT

(71) Applicant: SCHOTT AG, Mainz (DE)

(72) Inventors: Frank Gindele, Schweitenkirchen (DE); Christian Rakobrandt, Landshut (DE)

(73) Assignee: SCHOTT AG, Mainz (DE)

( * ) Notice: Subject to any disclaimer, the term of this patent is extended or adjusted under 35 U.S.C. 154(b) by 670 days.

(21) Appl. No.: 17/103,217

(22) Filed: Nov. 24, 2020

(65) Prior Publication Data

US 2021/0080100 A1  Mar. 18, 2021

Related U.S. Application Data

(62) Division of application No. 15/060,866, filed on Mar. 4, 2016, now Pat. No. 10,890,318.

(30) Foreign Application Priority Data

Mar. 6, 2015 (DE) .......................... 102015103331.3
Mar. 10, 2015 (DE) .......................... 102015103507.3

(51) Int. Cl.
*F21V 33/00* (2006.01)
*A61B 1/06* (2006.01)
(Continued)

(52) U.S. Cl.
CPC ........ *F21V 33/0068* (2013.01); *A61B 1/0684* (2013.01); *A61C 1/088* (2013.01); *A61C 3/02* (2013.01); *F21K 9/20* (2016.08); *F21K 9/90* (2013.01); *F21V 3/00* (2013.01); *F21V 17/101* (2013.01); *F21V 31/00* (2013.01); *H01L 25/167* (2013.01); *H01L 33/005* (2013.01); *F21W 2131/20* (2013.01); *F21Y 2101/00* (2013.01);
(Continued)

(58) Field of Classification Search
None
See application file for complete search history.

(56) References Cited

U.S. PATENT DOCUMENTS 4,686,324 A * 8/1987 Debaisieux .......... H05K 5/0095
                                                                 174/17.05
5,531,664 A    7/1996 Adachi
(Continued)

FOREIGN PATENT DOCUMENTS

CN   102628554         8/2012
DE   102004061551 A1   7/2005
(Continued)

OTHER PUBLICATIONS

Schott Press Release, "The first ring-shaped autoclavable High Brightness LEDs SCHOTT" Landshut, Germany, Feb. 9, 2015, with English machine translation.
(Continued)

*Primary Examiner* — Hsien Ming Lee
(74) *Attorney, Agent, or Firm* — Ruggiero McAllister & McMahon LLC

(57) ABSTRACT

A hermetically sealed LED light is provided that includes a ceramic base with a plurality of LEDs and a metal cap soldered thereto and a channel for introducing an electrical, optical, or mechanical component.

21 Claims, 5 Drawing Sheets

(51) Int. Cl.
*A61C 1/08* (2006.01)
*A61C 3/02* (2006.01)
*F21K 9/20* (2016.01)
*F21K 9/90* (2016.01)
*F21V 3/00* (2015.01)
*F21V 17/10* (2006.01)
*F21V 31/00* (2006.01)
*H01L 25/16* (2023.01)
*H01L 33/00* (2010.01)
*F21W 131/20* (2006.01)
*F21Y 101/00* (2016.01)

(52) U.S. Cl.
CPC ............... *H01L 2224/48091* (2013.01); *H01L 2933/0033* (2013.01)

(56) References Cited

U.S. PATENT DOCUMENTS

| | | | |
|---|---|---|---|
| 6,547,721 | B1 | 4/2003 | Higuma |
| 6,607,384 | B1 | 8/2003 | Nakanishi |
| 6,796,939 | B1 | 9/2004 | Hirata |
| 8,308,637 | B2 | 11/2012 | Ishigami |
| 8,480,572 | B2 | 7/2013 | Ishigami |
| 8,801,255 | B2 | 8/2014 | Kudo |
| 2004/0176661 | A1 | 9/2004 | Futatsugi |
| 2005/0142514 | A1 | 6/2005 | Scott |
| 2006/0058584 | A1 | 3/2006 | Hirata |
| 2007/0191684 | A1 | 8/2007 | Hirata |
| 2007/0205419 | A1 | 9/2007 | Ono |
| 2008/0045802 | A1 | 2/2008 | Brandstaetter |
| 2008/0068862 | A1 | 3/2008 | Shimura |
| 2008/0158349 | A1 | 7/2008 | Miller |
| 2008/0193087 | A1* | 8/2008 | Ishida .................. G02B 6/3874 385/84 |
| 2010/0164346 | A1* | 7/2010 | Li ............................ F21V 7/06 313/46 |
| 2010/0214768 | A1 | 8/2010 | Dixon |
| 2011/0070553 | A1 | 3/2011 | Stempfle |
| 2011/0186896 | A1* | 8/2011 | Loh ....................... H01L 33/641 257/E33.072 |
| 2014/0134568 | A1* | 5/2014 | Heinrich ................. A61M 3/02 433/29 |
| 2014/0210368 | A1 | 7/2014 | Lee |
| 2014/0339710 | A1 | 11/2014 | Fujiwara |
| 2015/0103856 | A1* | 4/2015 | Hagino ............... H01S 5/02345 372/44.01 |
| 2015/0263243 | A1* | 9/2015 | Nakagawa ........... H01L 33/505 257/98 |
| 2015/0372200 | A1* | 12/2015 | Seko ....................... F21S 41/16 362/510 |
| 2016/0190407 | A1 | 6/2016 | Ahn |
| 2016/0195706 | A1 | 7/2016 | Fijii |
| 2019/0029494 | A1 | 1/2019 | Araki |

FOREIGN PATENT DOCUMENTS

| | | |
|---|---|---|
| DE | 202005002341 U1 | 7/2005 |
| DE | 202005020300 U1 | 2/2006 |
| DE | 102007022605 A1 | 11/2007 |
| DE | 202010000518 U1 | 8/2011 |
| EP | 2548530 | 1/2013 |
| EP | 2815719 | 12/2014 |
| EP | 2842513 | 3/2015 |
| JP | H09140664 | 6/1997 |
| JP | 2000316874 | 11/2000 |
| JP | 2002511775 | 4/2002 |
| JP | 2003163382 | 6/2003 |
| JP | 2004355852 | 12/2004 |
| JP | 2005215213 | 8/2005 |
| JP | 2006223763 | 8/2006 |
| JP | 2007266568 | 10/2007 |
| JP | 2009272576 | 11/2009 |
| JP | 2011097984 | 5/2011 |
| JP | 2011100866 | 5/2011 |
| JP | 2013251384 | 12/2013 |
| JP | 2015003025 | 1/2015 |
| JP | 2015002824 A | 8/2015 |
| KR | 101373710 | 3/2014 |
| WO | 9515060 A1 | 6/1995 |
| WO | 9814527 | 4/1998 |

OTHER PUBLICATIONS

Indium Corporation, Eutectic Gold Sin (AuSn), Sep. 22, 2009, Indium Corporation, Accessed May 13, 2019 (Year: 2009).

\* cited by examiner

HERMETICALLY SEALED LED LIGHT AND METHOD FOR MANUFACTURING A HERMETICALLY SEALED LED LIGHT

CROSS REFERENCE TO RELATED APPLICATIONS

This application is a divisional of U.S. application Ser. No. 15/060,866 filed on Mar. 6, 2016, which claims benefit under 35 USC § 119(a) of German Patent Application No. 102015103331.3 filed Mar. 6, 2015 and German Patent Application No. 102015103507.3 filed Mar. 10, 2015, the entire contents of all of which are incorporated herein by reference.

BACKGROUND OF THE INVENTION

1. Field of the Invention

The invention relates to a hermetically sealed LED light and a method for manufacturing a hermetically sealed LED light. More particularly, the invention relates to an LED light which is used in the medical field, that is, for medical devices and instruments.

2. Description of Related Art

In the medical field, especially in equipment for dentists, LED lights are increasingly utilized and may in particular even be part of medical instruments. They are used for illumination purposes, for example for illuminating the oral cavity of a patient, for detecting defect sites, such as caries, for example when light of a certain wavelength is emitted which facilitates the identification of defect sites, as a camera light, in particular of an endoscope, and for curing filling materials, for instance curing of curable plastics using UV light.

Typically, such lights are subject to high loads. In particular, most medical devices have to be hermetically sealed and even autoclavable in some cases.

Moreover, the utilized devices should be durable and must not give off any harmful substances.

In particular, dental instruments handles are known that comprise an LED light source. The LED light source is mostly integrated in the housing of the handle, and the light emitted by the LED light source is directed, by means of a light guide, to a window in the front-end region of the handle, from where it radiates into the oral cavity.

Known LED lights which are sealed by means of a polymeric potting compound, for example, are usually not sufficiently suitable for being used with a medical device at least not on the outside thereof.

SUMMARY

Therefore, the invention is based on the object of providing a hermetically sealed LED light which is well suited to be integrated into a medical instrument and which is able to meet the elevated demands in the medical field in terms of durability and tightness.

The object of the invention is achieved by a hermetically sealed LED light and a method for manufacturing a hermetically sealed LED light.

The invention relates to a hermetically sealed LED light, that is an LED light with a housing that is at least liquid-tight.

The LED light comprises a base with a plurality of LEDs.

Preferably, the LEDs are implemented in form of an LED chip directly bonded to the base.

Such LED chips may comprise high power LEDs, heat is readily dissipated via the base, and the components are compact.

The base is made of a ceramic material. In particular, the base is made of an aluminum oxide and/or an aluminum nitride.

Furthermore, the LED light comprises a metal cap having at least one window. Preferably, the metal cap has a plurality of windows, a respective one in front of each LED, through which the light exits from the LED light.

The metal cap is soldered to the base, and the LED light furthermore comprises a channel extending both through the base and through the cap, for introducing an electrical, optical, and/or mechanical component.

By combining a ceramic base with a metal cap soldered thereto, it was possible to provide a unit in the form of an LED light that exhibits high density, despite of a channel extending through the components.

The channel serves to accommodate an electrical or mechanical component, which in particular is part of an employed medical device.

For example, an image sensor and in particular a camera may be arranged in the channel, for which the LED light is used as a light source.

The channel may have any shape, in particular a conical, circular cylindrical, or polygonal shape. It is also conceivable to provide a stepped channel, for example by having different diameters of the channel in the base and in the cap. Such a step may then serve as a stop for better retaining a mechanical or electrical component.

In a preferred embodiment, the LED light has an annular shape and the channel is arranged substantially centrally.

The LEDs are preferably distributed over the periphery of the so formed ring. The LED light may in particular comprise 4 to 10 LEDs.

Such a light may in particular be arranged on a headpiece of a medical instrument, for example a dentist's drilling device. In this case, the drive shaft of the drill and/or the drilling device itself may extend through the channel, and the LEDs are in particular used for illumination purposes.

Preferably, the LED light comprises a plurality of windows which are distributed annularly.

In one refinement of the invention, the windows are defined by lenses.

In particular, the light of the LEDs may be focused by the windows.

In a preferred embodiment, each of the windows is arranged in a respective channel of the metal cap. The channels in which the windows are arranged preferably have a height between 0.15 and 20 mm. Preferably, the channels each extend until the base, that means that immediately adjacent to a respective channel the metal cap is soldered to the base.

In particular, it is contemplated that the metal cap preferably has channels of a cylindrical, in particular circular cylindrical shape into which glass windows in the form of lenses have been fused.

For manufacturing such a metal cap, a portion of a glass rod may be introduced into each channel. When being heated, the glass melts and due to the surface tension of the glass a lens is formed.

In one embodiment, the LED light comprises a plurality of windows, and the metal cap has a depression adjacent to each of the windows.

In particular, the metal cap has a depression at its upper surface adjacent to a channel.

If now a glass window is fused into the channel so that a lens is formed, due to the depression the lens will not protrude from the upper surface of the metal cap, so that when the LED light is used without further protective glass, the windows will not be damaged when an object is contacted because the metal cap will abut thereon.

In one embodiment of the invention, a converter is arranged in the channel below the window. In particular, a converter with a silicone carrier matrix may be used in which fluorescent particles, such as phosphorus, YAG, etc. are embedded. The converter can be mounted in the channel particularly easily, for example by adhesive bonding. The use of a silicone matrix converter results in simple manufacturing and high temperature stability. The use of converters with an inorganic matrix is conceivable as well.

By fusing a glass window into a channel and preferably arranging the glass window as close as possible in front of an optionally employed converter, is possible to provide an LED light with a wide beam or emission angle.

In particular, the emission angle can be greater than 85°, preferably greater than 90°, and more preferably greater than 94°. In the context of the invention, emission angle refers to the angle included between lateral points of half maximum intensity.

The invention furthermore relates to a hermetically sealed LED light, in particular a light such as described above.

Such a light comprises a base, preferably a ceramic base, with a plurality of LEDs, and with at least one cap having a plurality of windows, and the LED light comprises separately controllable LEDs of different light colors, and the light emission angle of at least two separately controllable LEDs is different.

Thus, the LED light comprises LEDs of different light color for different applications. In case an LED light is provided for the dental field, these may for example comprise LEDs with substantially white light for illuminating the oral cavity, LEDs of a special light color for detecting caries or dental plaque, and LEDs emitting UV light which are used to cure resins. These LEDs can be controlled independently. For this purpose, the base has a plurality of electrical feedthroughs for the respective LEDs or LED sets.

It is in particular contemplated that at least one LED has an emission angle of less than 60° and another LED has an emission angle of more than 70°. Furthermore, it is in particular contemplated that the emission angles of at least two LEDs differ by at least 10°, preferably by at least 20°.

For this purpose, preferably, windows are used that are defined by lenses having different focal lengths and/or different aperture angles.

If they are formed by melting glass into the channels, such lenses may for example be provided by a different shape of the channel and/or by a different glass.

For LEDs that emit UV light, for example, focusing of the light and emission with a small emission angle can be useful, whereas LEDs for illuminating the oral cavity will have a wider emission angle.

The LED light is in particular part of a medical instrument, and the LED light is integrated in the medical instrument in such a manner that the LED light directly radiates to the outside. This is to say that the light is not guided to an exit window via a light guide. However, it is conceivable that another window or protective glass is provided in the emission direction. Preferably, however, the metal cap of the light with its windows defines the termination of the medical instrument.

The invention further relates to a method for manufacturing an LED light, in particular to a method for manufacturing an LED light as described above.

First, an LED is assembled on a ceramic base, in particular an LED which is arranged on a chip. Then, a metal cap is soldered to the base using a metal solder.

Preferably, at least one window is provided in the metal cap already before the soldering step, in particular by melting or fusing a glass into a respective channel of the metal cap.

It is also conceivable to provide the at least one window in the form of a compression glass-to-metal seal.

The windows made of glass are preferably formed of a material having good chemical resistance, in particular a silicate glass, e.g. a borosilicate glass.

Then, the only thing that remains to do is to join the components metal cap with window and ceramic base.

It has been found that when using a suitable solder, in particular when using a gold-tin solder, a stable and hermetically sealed connection can be achieved without the LED light getting so hot that the LED, especially in the form of an LED chip, risks to be damaged.

By using a gold-tin solder it is possible to provide an autoclavable housing.

Furthermore, this connection is stable even during any subsequent soldering processes, in particular a reflow process, or when a tin-silver-copper solder is used.

Preferably, a solder, in particular a gold-tin solder, is used that has a melting temperature below 300° C., more preferably below 280° C.

Furthermore, the ceramic base preferably has electrical feedthroughs which are hermetically sealed by a metal solder.

These feedthroughs through which the LEDs are electrically connected, are preferably also formed prior to solder-connecting the base and the metal cap.

According to one refinement of the invention, at least the metal cap is provided with a coating, in particular with a nickel and/or gold containing coating. In particular, a hard gold coating is applied.

The metal cap is preferably made of a stainless steel, in particular a stainless steel having a low coefficient of thermal expansion. Thus, the metal cap is adapted to the low thermal expansion coefficient of the ceramic. In particular, the material of the metal cap has a thermal expansion coefficient a at room temperature of less than 15 ppm/K, preferably less than 8, and more preferably less than 5 ppm/K.

In particular, the metal cap is made of a ferritic stainless steel.

In one embodiment of the invention, the coefficients of thermal expansion a of the metal cap and of the material of the windows differ by less than 5 ppm/K, preferably by less than 1 ppm/K from each other. The same preferably applies to the coefficients of thermal expansion of the base and of the metal cap.

Solders that may be used for the feedthroughs for electrically connecting the LEDs include gold-tin, tin, copper, and silver solders, for example.

The invention allows to provide a hermetically sealed LED light which is even autoclavable.

BRIEF DESCRIPTION OF THE DRAWINGS

The subject matter of the invention will now be explained with reference to exemplary embodiments.

DETAILED DESCRIPTION

Figure 1:
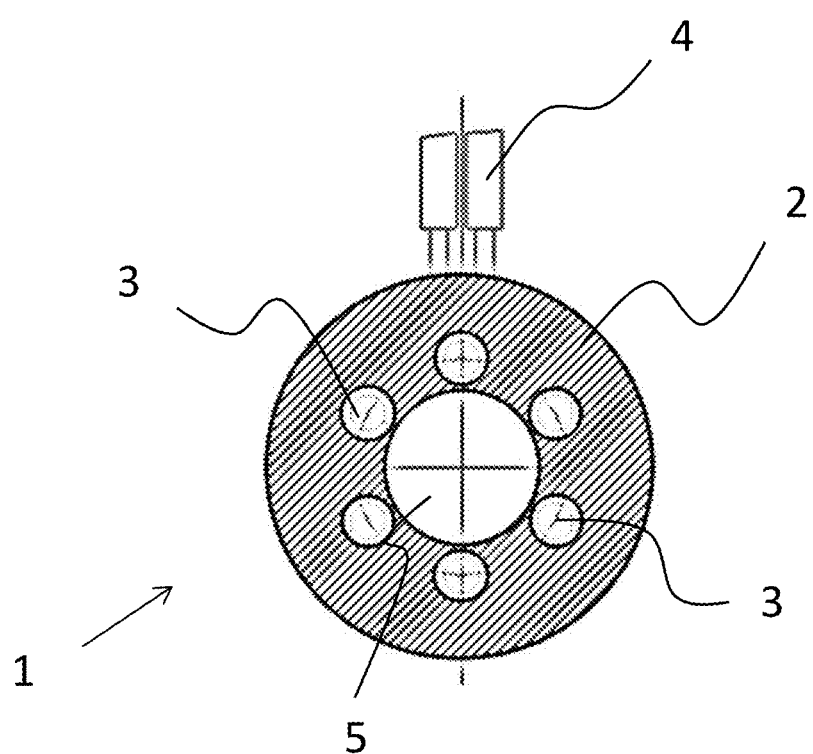
FIG. 1 shows a plan view of an exemplary embodiment of a hermetically sealed LED light.

FIG. 1 shows a plan view of an exemplary embodiment of a hermetically sealed LED light 1 according to the invention.

In this embodiment, the LED light 1 has an annular shape. On the top, metal cap 2 can be seen which has a plurality of windows 3 through which the light from the underlying LEDs is emitted.

LED light 1 can be connected via supply line 4.

The six windows 3 illustrated in this exemplary embodiment are distributed circumferentially across the LED light 1.

Furthermore, a central channel 5 with a circular cross section can be seen, which is intended to accommodate an electrical, optical, or mechanical component.

Figure 2:
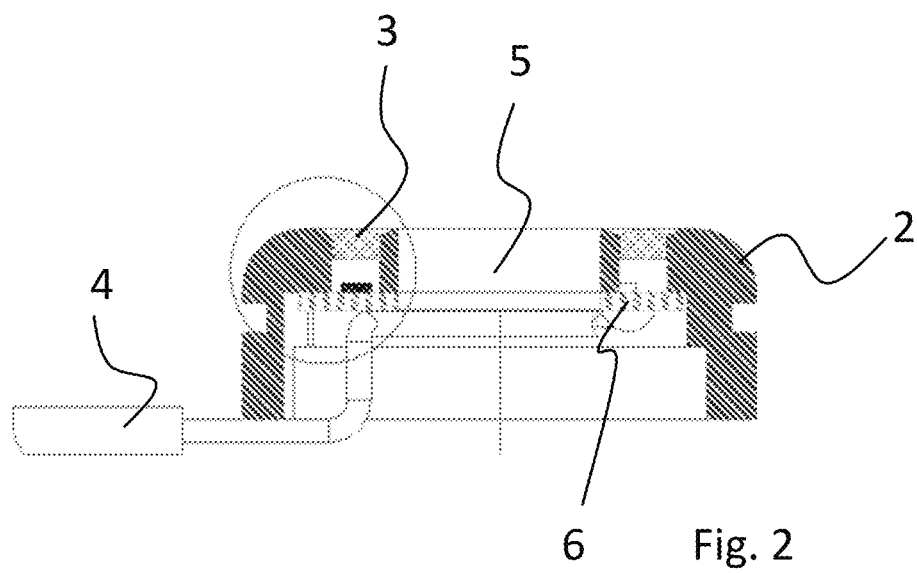
FIG. 2 is a sectional view of FIG. 1.

FIG. 2 shows a sectional view of the LED light illustrated in FIG. 1.

It can be seen that the metal cap 2 which is made of a stainless steel, is cup-shaped.

A base 6 made of a ceramic material, in particular of aluminum oxide, is mounted in the cup-shaped metal cap 2 from the bottom side and is soldered to the metal cap by means of a gold-tin solder.

The plate-shaped base 6 is likewise annular, so that channel 5 extends both through the base 6 and through the metal cap 2.

Base 6 has feedthroughs (not shown), through which current for driving the LEDs is supplied to the upper side, via supply line 4.

Figure 3:
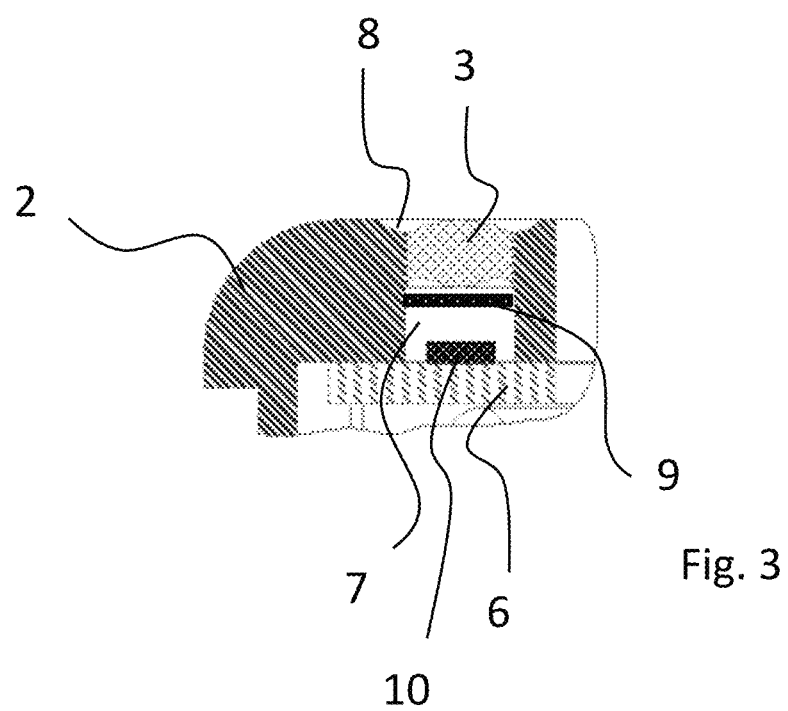
FIG. 3 illustrates a detail of FIG. 2.

FIG. 3 illustrates a detail of FIG. 2, namely the region in which a window 3 is arranged.

It can be seen that below window 3 the base 6 is equipped with an LED 10. LED 10 is implemented in form of a chip, in particular as a surface mounted device (SMD).

On the upper side of base 6 supply lines may be provided, for example in the form of flat conductive traces (not shown) for electrically connecting the LED 10.

As can further be seen, window 3 is provided in form of a lens.

Window 3 is arranged in a channel 7 which in turn extends through metal cap 2.

The lenticular shape of window 3 is caused by the surface tension of the glass, being produced by inserting a glass rod into channel 7 and then melting it.

At the upper end of channel 7 a peripheral depression 8 is provided.

Due to depression 8, the window 3 in form of a lens does not protrude.

Optionally, depending on the light color that is desired, a converter 9 may be arranged in channel 7. This may in particular be a converter with a silicone matrix, which is adhesively bonded into channel 7.

It can furthermore be seen that the upper surface of base 6 is soldered to the lower surface of cup-shaped metal cap 2.

The edge of base 6 is spaced from metal cap 2 in this embodiment.

By connecting base 6 and metal cap 2 by soldering and by melting the window 3 into the channel, a hermetic seal of the LED 10 is provided.

Feedthroughs in the base 6 are preferably filled with a solder as well.

For assembling the LED light according to the invention, first the metal cap is produced with the windows fused into it, and separately therefrom the base 6 is equipped with LEDs 10.

These two main components are then soldered together using a gold-tin solder that has a melting temperature below 340° C., preferably below 325° C., more preferably below 300° C.

The method of the invention is not only suitable for the annular LED light illustrated herein, but also for other types of lights, in particular lights that do not have a central channel.

Figure 4:
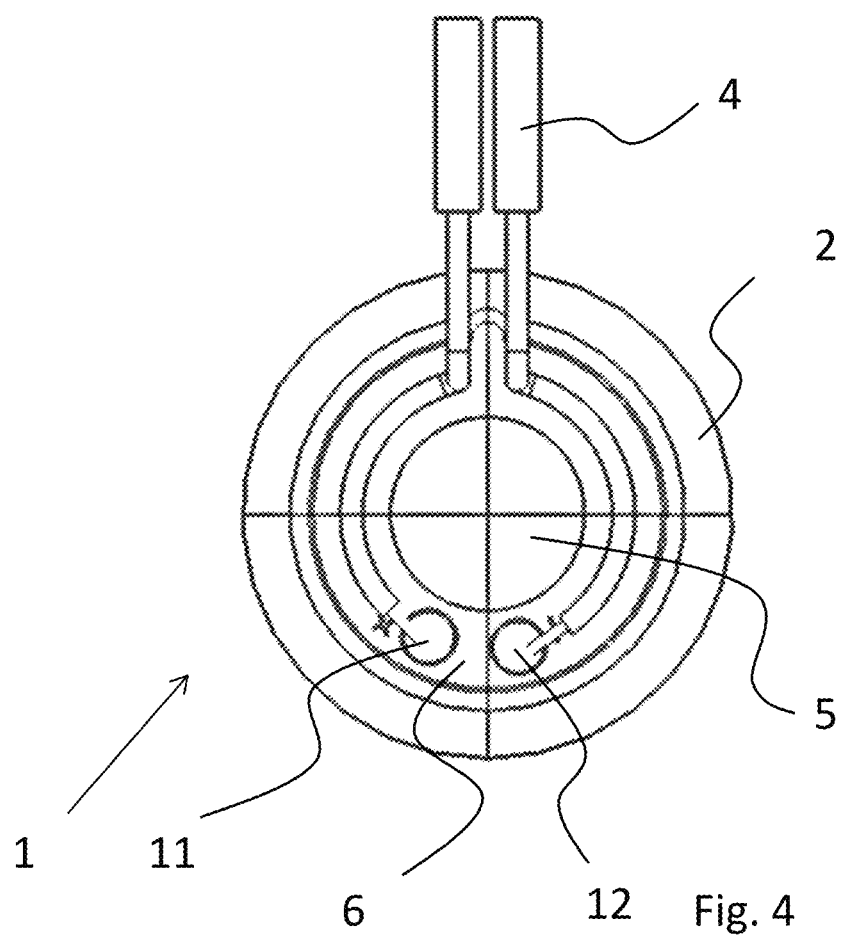
FIG. 4 shows a bottom plan view.

FIG. 4 shows a bottom plan view of LED light 1.

Annular base 6 can be seen which in this exemplary embodiment has feedthroughs 11 and 12 via which the LEDs on the upper surface are driven.

Base 6 is embedded in cup-shaped metal cap 2.

Further, central channel 5 can be seen, in which an electrical, optical, or mechanical component may be arranged.

Supply lines 4 extend around channel 5 on the bottom surface.

It will be understood that an LED light that has a plurality of separately controlled LEDs typically will comprise more than the two feedthroughs for the positive and negative terminals as illustrated herein. That is because the driver circuits for driving the LEDs are preferably not arranged in the hermetically sealed portion of the light illustrated herein, but are rather arranged externally.

Figure 5:
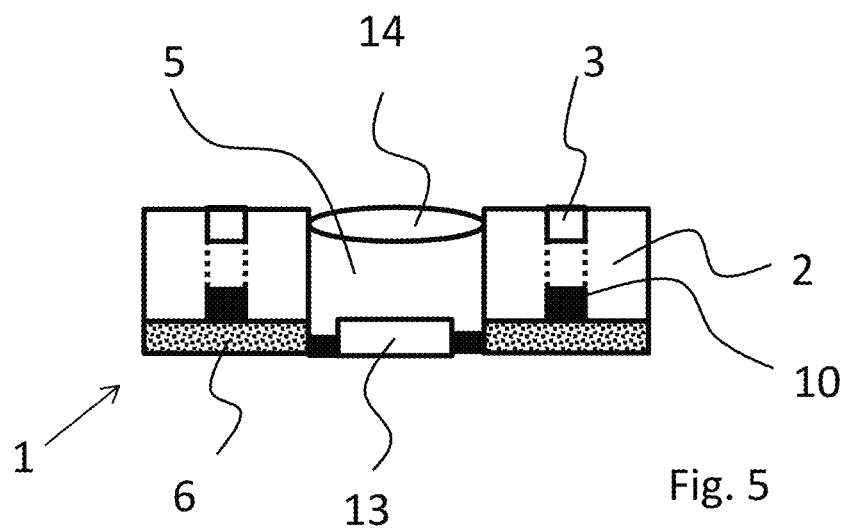
FIG. 5 is a schematic view illustrating the use of the hermetically sealed LED light according to the invention in conjunction with an image sensor.

FIG. 5 schematically shows a hermetically sealed LED light 1 which, again in this embodiment, comprises an annular ceramic base 6 to which a likewise annular metal cap is soldered, which has a plurality of windows 3 through which the light from LEDs 10 radiates to the outside.

In the central channel 5, an image sensor 13 and a lens 14 is arranged.

Figure 6:
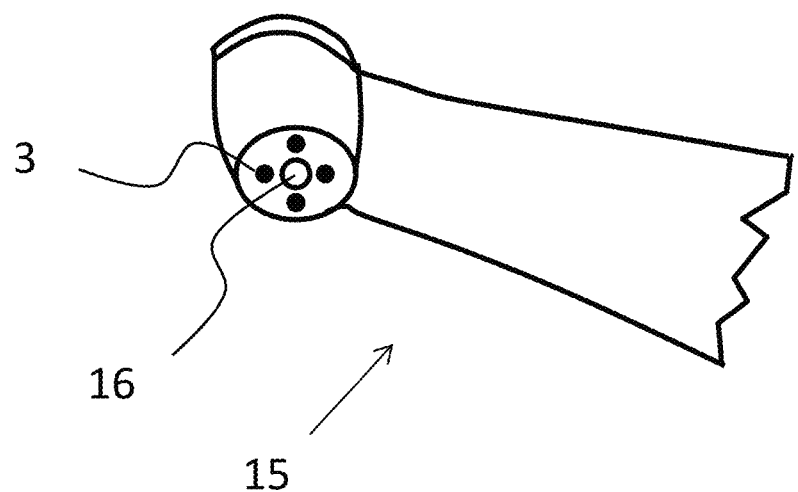
FIG. 6 is a schematic view of a medical instrument with a hermetically sealed LED light according to the invention integrated therein.

FIG. 6 is a schematic view of a medical instrument, especially of the head piece of a dental drilling device.

A receptacle 16 can be seen, into which the drills are inserted so as to be connected to a drive shaft.

A hermetically sealed LED light according to the invention is directly mounted on the head of the medical instrument 15, and the light therefrom is directly emitted to the outside, through windows 3.

Because of the good sealing of the housing of the inventive light it is not necessary for the LED light to be arranged in the housing of the medical instrument and to guide the emitted light to the front end by means of light guides.

Figure 7:
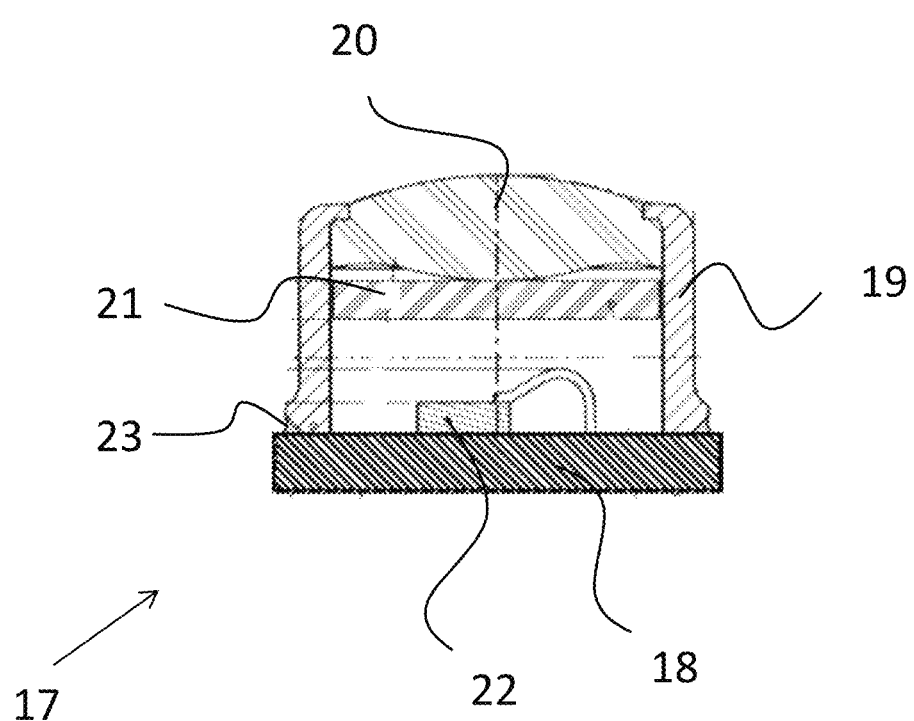
FIG. 7 shows another exemplary embodiment of a hermetically sealed LED light that is not annular.

FIG. 7 shows an embodiment of a hermetically sealed LED light which does not have an annular configuration but was produced by the method according to the invention.

The LED light 17 comprises a base 18 made of a ceramic material, in particular aluminum oxide, to which a metal cap 19 in particular made of stainless steel has been soldered using a gold-tin solder.

The base 18 is not arranged within the cap 19 but is mounted to an end face thereof.

Metal cap 19 has a beveled edge. The solder 23 in the resulting gap provides for a better bond between the components.

Inside the hermetically sealed LED light 19, an LED 22 configured as a chip is disposed, and the light therefrom is first incident on an overlying converter 21 which is arranged below window 20 in the form of a lens.

For manufacturing this LED light 17, again, a window 20 is first produced from glass by melting the glass into the metal cap 19. Optionally, converter 21 is additionally assembled in the metal cap 19.

Then, metal cap 19 is soldered to base 18 comprising the already assembled LED 22.

LIST OF REFERENCE NUMERALS

1 LED light
2 Metal cap
3 Window
4 Supply line
5 Channel
6 Base
7 Channel
8 Depression
9 Converter
10 LED
11 Feedthrough
12 Feedthrough
13 Image Sensor
14 Lens
15 Medical instrument
16 Receptacle
17 LED light
18 Base
19 Metal cap
20 Window
21 Converter
22 LED
23 Solder

What is claimed is:

1. A method for manufacturing a hermetically sealed LED light, comprising:
    assembling at least one LED on a base made of ceramic;
    providing a metal cap having an end with an opening surrounded by a peripheral depression;
    melting a glass into the opening to define a window in the opening, the window having a a lenticular shape due to surface tension of the glass that does not protrude beyond the end of the metal cap; and
    soldering the metal cap to the base using a metal solder so that the at least one LED is within the metal cap.

2. The method of claim 1, wherein the metal solder comprises a gold-tin solder is used for soldering the metal cap to the base.

3. The method of claim 1, wherein the metal cap and the window have coefficients of thermal expansion that differ by less than 5 ppm/K.

4. The method of claim 1, wherein the metal cap and the window have coefficients of thermal expansion that differ by less than 1 ppm/K.

5. The method of claim 1, wherein the metal cap is coated with a nickel and/or gold containing coating.

6. The method of claim 1, wherein the window does not extend into the peripheral depression.

7. A method for manufacturing a hermetically sealed LED light, comprising:
    providing a metal cap having an end face at one end, an opening at an opposite end, a hollow channel therebetween, and a peripheral depression at the opposite end of the metal cap;
    melting a glass into the metal cap at the opening to form a hermetically sealed window in the opening, the window having a lenticular shape due to surface tension of the glass that does not protrude beyond the opposite end of the metal cap;
    providing a base made of a ceramic material;
    disposing an LED chip on an upper surface of the base;
    arranging the metal cap with respect to the base so that the base is not arranged within the hollow channel but is mounted to the end face of the metal cap with the LED chip in the hollow channel; and
    soldering, with a solder, an outer edge of the end face and the upper surface of the base to one another to hermetically seal the metal cap and the base to one another.

8. The method of claim 7, wherein the metal cap and the window have coefficients of thermal expansion that differ by less than 5 ppm/K.

9. The method of claim 7, wherein the metal cap and the window have coefficients of thermal expansion that differ by less than 1 ppm/K.

10. The method of claim 7, further comprising arranging a converter in the hollow channel between the window and the LED chip.

11. The method of claim 10, wherein the converter is an inorganic matrix.

12. The method of claim 10, wherein the converter is silicone matrix comprising embedded fluorescent particles.

13. The method of claim 10, further comprising adhesively bonding the converter into the hollow channel.

14. The method of claim 10, wherein the step of arranging the converter in the hollow channel comprises arranging the converter next to the window.

15. The method of claim 7, wherein the window is a lens.

16. The method of claim 7, further comprising:
    bevelling the outer edge of the end face; and
    arranging the metal cap with respect to the base so that the bevelling of the outer edge results in a gap between the outer edge and the upper surface; and
    filling the gap with the solder.

17. The method of claim 7, wherein the ceramic material is made of a material selected from a group consisting of aluminum oxide, aluminum nitride, and combinations thereof.

18. The method of claim 7, wherein the metal cap is a stainless-steel metal cap.

19. The method of claim 7, wherein the solder is gold-tin solder.

20. The method of claim 7, wherein the step of melting the glass into the metal cap at the opening comprises:
    inserting a glass rod into the hollow channel; and
    melting the glass rod.

21. The method of claim 7, wherein the window does not extend into the peripheral depression.

* * * * *